(12) United States Patent
Bertling

(10) Patent No.: US 6,803,021 B1
(45) Date of Patent: Oct. 12, 2004

(54) DEVICE FOR RECEIVING AND DISCHARGING A GIVEN AMOUNT OF LIQUID

(75) Inventor: Wolf Bertling, Erlangen (DE)

(73) Assignee: November AG Novus Medicatus Bertling Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/647,618

(22) PCT Filed: Mar. 31, 1999

(86) PCT No.: PCT/DE99/01052

§ 371 (c)(1),
(2), (4) Date: Oct. 3, 2000

(87) PCT Pub. No.: WO99/51350

PCT Pub. Date: Oct. 14, 1999

(30) Foreign Application Priority Data

Apr. 3, 1998 (DE) ..................... 298 06 142 U

(51) Int. Cl.[7] .............. B01L 3/02; G01N 1/10
(52) U.S. Cl. ............. 422/100; 422/100; 436/180; 75/863.32; 75/864; 75/864.01; 75/864.11
(58) Field of Search .......... 422/100; 436/180; 73/863.32, 864, 864.01, 864.02, 864.11, 864.72, DIG. 1

(56) References Cited

U.S. PATENT DOCUMENTS

| | | | | |
|---|---|---|---|---|
| 694,530 A | * | 3/1902 | Comer | 116/227 |
| 898,456 A | * | 9/1908 | Farnham | 141/110 |
| 2,104,325 A | * | 1/1938 | Juffa | 366/130 |
| 2,423,173 A | * | 7/1947 | Brady et al. | 210/446 |
| 2,965,255 A | * | 12/1960 | Gerarde | 206/220 |
| 2,982,987 A | * | 5/1961 | Knapp | 401/139 |
| 3,748,909 A | * | 7/1973 | Kuo | 422/100 |
| 3,772,154 A | | 11/1973 | Isenberg et al. | 435/33 |
| 3,780,992 A | | 12/1973 | Nishi et al. | 366/114 |
| 3,834,241 A | * | 9/1974 | Garren et al. | 222/209 |
| 4,022,576 A | * | 5/1977 | Parker | 422/100 |
| 4,212,204 A | * | 7/1980 | St. Amand | 222/209 |
| 4,309,912 A | * | 1/1982 | Smith | 222/133 |
| 4,563,332 A | * | 1/1986 | Mitchell et al. | 422/100 |
| 4,589,421 A | * | 5/1986 | Ullman | 422/100 |
| 4,808,381 A | * | 2/1989 | McGregor et al. | 215/307 |
| 4,877,585 A | * | 10/1989 | Perlman | 422/100 |
| 5,073,347 A | * | 12/1991 | Garren et al. | 422/100 |
| 5,125,278 A | * | 6/1992 | Foldenauer | 422/922 |
| 5,232,669 A | * | 8/1993 | Pardinas | 206/562 |
| 5,364,596 A | | 11/1994 | Magnussen et al. | 422/100 |
| 5,406,856 A | * | 4/1995 | Kuhn | 73/864.11 |
| 5,460,782 A | * | 10/1995 | Coleman et al. | 422/100 |
| 5,697,522 A | * | 12/1997 | Mayes | 222/1 |
| 5,717,054 A | | 2/1998 | Schultz | 528/100 |
| 5,775,546 A | * | 7/1998 | Buehler | 222/209 |
| 5,795,789 A | | 8/1998 | Dietzen | 436/500 |
| 5,801,062 A | * | 9/1998 | Sarstedt et al. | 436/180 |
| D401,698 S | * | 11/1998 | Daniels | 73/864.01 |
| 5,844,686 A | | 12/1998 | Treptow et al. | 356/440 |
| 5,964,782 A | * | 10/1999 | Lafontaine et al. | 606/213 |
| 5,972,613 A | | 10/1999 | Somack et al. | 435/6 |
| 6,030,582 A | * | 2/2000 | Levy | 215/247 |

FOREIGN PATENT DOCUMENTS

| | | |
|---|---|---|
| DE | 29 01 827 | 12/1980 |
| DE | 30 16 594 A | 11/1981 |
| DE | 88 03 331.7 | 4/1988 |
| DE | 37 01 250 A1 | 7/1988 |
| DE | 92 00 604.3 | 3/1992 |

* cited by examiner

Primary Examiner—Jill Warden
Assistant Examiner—Brian R Gordon
(74) Attorney, Agent, or Firm—Pearne & Gordon LLP

(57) ABSTRACT

The invention relates to a device for receiving and discharging a given amount of liquid, comprising agitating means (2) arranged on one end (E1) of a capillary (1) and a diaphragm (3) in the vicinity of the other end (E2).

9 Claims, 2 Drawing Sheets

DEVICE FOR RECEIVING AND DISCHARGING A GIVEN AMOUNT OF LIQUID

BACKGROUND OF THE INVENTION

The invention relates to a device for taking up and discharging a defined amount of liquid.

G 88 03 331.7 discloses a pipette, in particular for use in dental technology. In this case, an agitating implement is attached to a suction tube. In the case of the known pipette, the liquid must be sucked into the suction tube by means of a suction device. The amount of liquid sucked in depends on the manner and method of actuation of the suction device. It can vary.

EP 0 569 851 A1 describes a pipetting device for the mixing of liquids. In this case, the pipette is connected to a take-up device connected to an eccentric. The device is complex and expensive. It requires, inter alia, a special vacuum line for sucking up the liquid to be pipetted.

JP Patent Abstracts of Japan: 07080331 A discloses a pipette tip with a radially peripheral cover formed onto it.

According to the prior art, a capillary produced from glass is also known for taking up a defined amount of blood. The blood taken up can be forced out of the capillary and transferred into a test tube by means of a rubber bellows or diaphragm which can be fitted onto the capillary. In said test tube, it is stirred with a reagent, usually with the aid of the capillary.

The fitting on of the bellows is laborious. Rupture of the capillary may occur as this takes place. The agitating action which can be produced by the capillary is inadequate.

SUMMARY OF THE INVENTION

The object of the invention is to eliminate the disadvantages of the prior art. In particular, a device for taking up and discharging a defined amount of liquid which is easy to handle and with which an improved agitating action can be achieved is to be specified.

According to the invention, the object is achieved by a device for taking up and discharging a defined amount of liquid, an agitating means being provided at a distal end of a capillary and a bellows being provided in the vicinity of a proximal end. The device according to the invention is easy to handle. There is no longer any need for a separate bellows to be pushed into the capillary. The agitating means which can be produced by the capillary is improved.

The bellows may have an aperture. This makes it possible for the liquid to be automatically sucked into the capillary. The liquid can be forced out of the capillary by keeping the aperture closed and squeezing the bellows.

The agitating means is expediently designed in the form of a hook-like continuation, which may have a tip. This simplifies and makes possible in particular the so-called "hooking" of blood.

According to a further design feature, the bellows may have an accordion-like arrangement of folds. This makes it easier to squeeze.

The capillary, the bellows and the agitating means may be produced in one piece from plastic. This makes production easier and less costly.

According to a further embodiment, the bellows may be formed onto a tubular receptacle, the tubular receptacle being able to taper in the direction of an opening lying opposite the bellows. A capillary produced from glass is expediently fitted frictionally into the tubular receptacle in the region of the opening. This two-part device is also easy to produce. It is possible here to resort to commercially available glass capillaries. The glass capillary is protected against the risk of rupture by being embedded in the tubular receptacle.

BRIEF DESCRIPTION OF THE SEVERAL VIEWS OF THE DRAWING

Further advantages of the invention are explained in more detail on the basis of the exemplary embodiments represented in the drawing, in which.

DETAILED DESCRIPTION OF THE INVENTION

Figure 1:
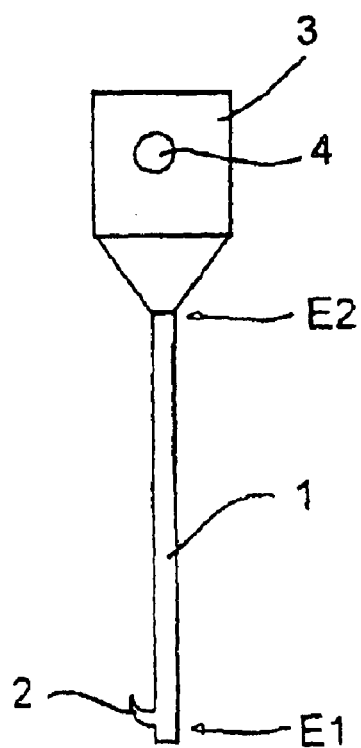
FIG. 1 shows a schematic side view of a first embodiment.
Figure 2:
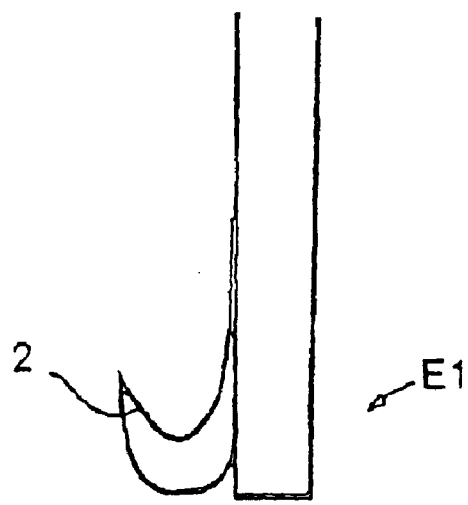
FIG. 2 shows a detailed view according to FIG. 1.

In FIGS. 1 and 2, a hook-like continuation 2 has been injection-moulded onto a distal end E1 of a capillary 1 produced from plastic. At a proximal end E2 there is a bellows 3 with an aperture 4. The bellows 3 may have accordion-like folds to make squeezing easier.

The capillary is designed such that it is suitable for taking up a defined amount of liquid, here for taking up 25 $\mu$l of blood. It is advantageously produced in a one-piece form from a transparent, biologically inert plastic of high rupture strength.

Figures 3, 4, 5:
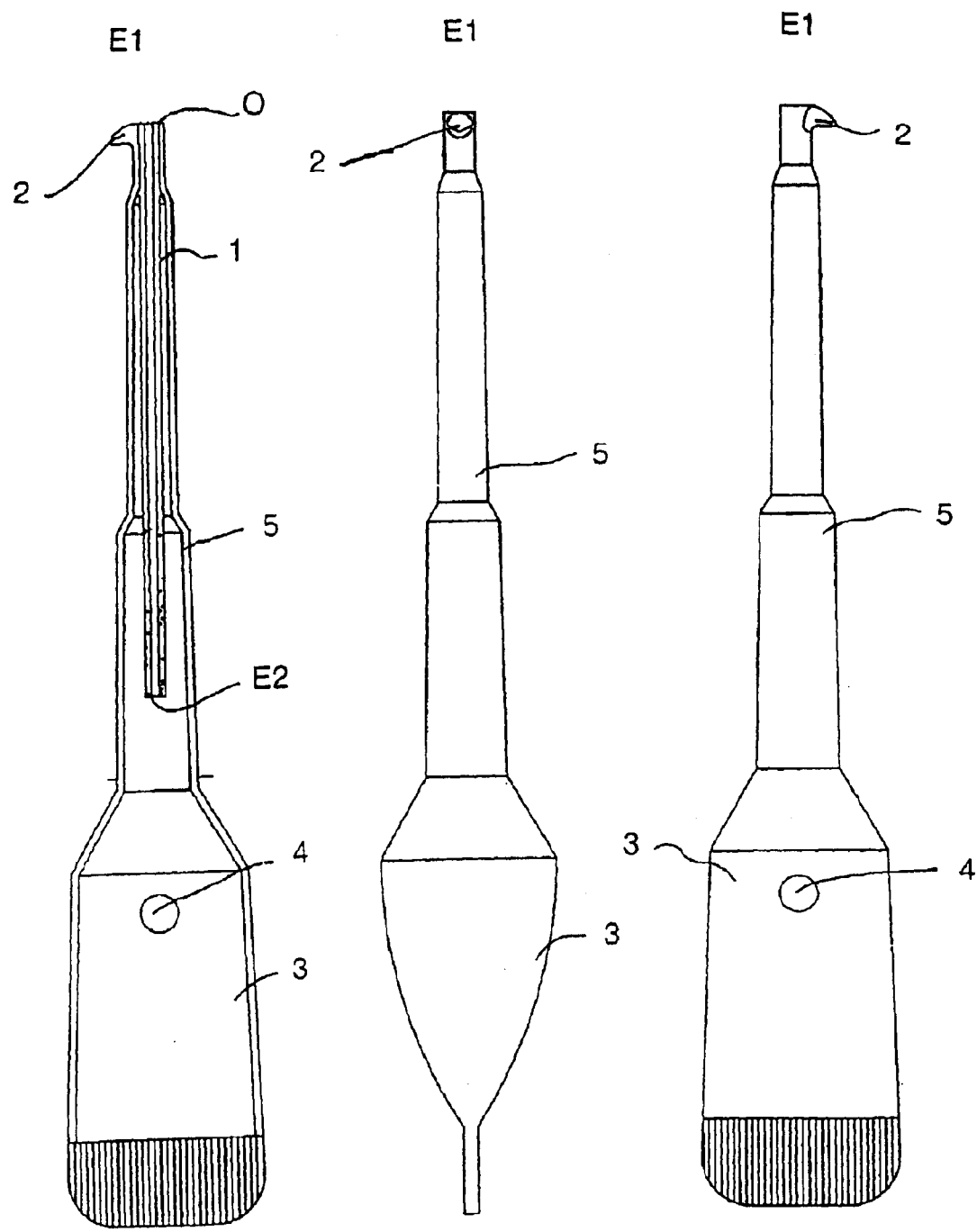
FIG. 3 shows a schematic cross-sectional view of a second embodiment.
FIG. 4 shows a first side view according to FIG. 3.
FIG. 5 shows a second side view according to FIG. 3.

A further exemplary embodiment is shown in FIGS. 3 to 5. Attached to a tube 5, tapering in steps in the direction of an opening O, is the bellows 3 at the proximal end E2 being opposite the opening O. In the vicinity of the opening O, the tube 5 has a diameter which allows a capillary 1 produced from glass to be received with a fractional fit. The hook-like continuation 2 is provided in the vicinity of the opening O. The bellows 3 and the hook-like continuation 2 are advantageously produced with the tube 5 in a one-piece form from injection-moulded plastic.

The function of the device is as follows:

For taking up liquid, for example blood, the distal end E1 of the capillary is brought into contact with the liquid. The liquid is taken up in the capillary 1, up to a certain height, by capillary forces. The capillary is advantageously filled completely with blood. The air displaced from the capillary 1 as this happens escapes via the aperture 4.

For discharging the liquid taken up in the capillary 1, the aperture 4 is closed, for example with the thumb. Pressure on the flexible bellows 3 causes the liquid to be forced out of the capillary 1.

The liquid can be effectively stirred with a reagent in a test tube by means of the hook-like continuation 2.

List of Designations 1 capillary
2 hook-like continuation
3 bellows
4 aperture
5 tube
E1 distal end
E2 proximal other end
O opening

What is claimed is:

1. Device for taking up and discharging a given amount of liquid, the device comprising agitating means for agitating the liquid, a capillary (1) having a proximal end (E2) and a distal end (E1), and a bellows (3) being provided in communication with said proximal end (E2) of the capillary, the agitating means comprising a hook located intermediate of the distal and proximal ends of the capillary.

2. Device according to claim 1, the bellows (3) having an aperture (4).

3. Device according to claim 2, the hook (2) having a tip.

4. Device according to claim 1 or 2, the bellows (3) having an accordion-like arrangement of folds.

5. Device according to claim 1 or 2, the capillary (1), the bellows (3) and the agitating means being produced in one piece from plastic.

6. Device according to claim 1 or 2, the bellows (3) being formed onto a tubular receptacle (5).

7. Device according to claim 6, the tubular receptacle tapering in the direction of an opening (O) lying opposite the bellows.

8. Device according to claim 7, the capillary being produced from glass and being fitted frictionally into the tubular receptacle (5) in the region of the opening (O).

9. An agitator for agitating a liquid comprising:

a capillary (1) having a distal end (E1) and a proximal end (E2);

a bellows (3) in communication with the proximal end (E2); and a hook intermediate the proximal end and the distal end (E1) of the capillary;

wherein the capillary and the bellow cooperate for taking up and discharging a given amount of the liquid.

* * * * *